(12) United States Patent
Cooper et al.

(10) Patent No.: US 9,629,420 B2
(45) Date of Patent: Apr. 25, 2017

(54) SYSTEMS AND METHODS FOR REDUCING FALSE NEGATIVE TAMPER DETECTION

(71) Applicant: BI Incorporated, Boulder, CO (US)

(72) Inventors: Larry T. Cooper, Longmont, CO (US); Donald A. Melton, Boulder, CO (US)

(73) Assignee: BI Incorporated, Boulder, CO (US)

( * ) Notice: Subject to any disclaimer, the term of this patent is extended or adjusted under 35 U.S.C. 154(b) by 0 days.

(21) Appl. No.: 14/531,735

(22) Filed: Nov. 3, 2014

(65) Prior Publication Data
US 2015/0131085 A1  May 14, 2015

Related U.S. Application Data

(60) Provisional application No. 61/902,754, filed on Nov. 11, 2013.

(51) Int. Cl.
*G01V 8/12* (2006.01)
*A44B 11/00* (2006.01)
*G01V 15/00* (2006.01)
*G01V 8/16* (2006.01)
*A61B 5/145* (2006.01)
*A61B 17/02* (2006.01)
*A61B 5/055* (2006.01)

(52) U.S. Cl.
CPC .............. *A44B 11/006* (2013.01); *G01V 8/16* (2013.01); *G01V 15/00* (2013.01); *A61B 5/055* (2013.01); *A61B 5/14532* (2013.01); *A61B 17/02* (2013.01); *Y10T 24/1368* (2015.01); *Y10T 29/49826* (2015.01)

(58) Field of Classification Search
CPC ........ A44B 11/006; G01V 15/00; G01V 8/16; Y10T 24/1368; Y10T 29/49826; A61B 17/02; A61B 5/14532; A61B 5/055

USPC .............. 385/76, 77, 78, 73, 70, 53, 54, 55; 439/157, 345, 620.26; 356/213, 222; 600/201, 310
See application file for complete search history.

(56) References Cited

U.S. PATENT DOCUMENTS

| | | | | |
|---|---|---|---|---|
| 5,123,071 A * | 6/1992 | Mulholland | ......... | G02B 6/3831 385/53 |
| 5,214,730 A * | 5/1993 | Nagasawa | ............ | G02B 6/3821 385/59 |
| 5,363,460 A * | 11/1994 | Marazzi | ............... | G02B 6/3825 385/55 |
| 5,420,951 A * | 5/1995 | Marazzi | ............... | G02B 6/3825 385/75 |
| 5,638,474 A * | 6/1997 | Lampert | ............. | G02B 6/3879 385/136 |
| 5,708,745 A * | 1/1998 | Yamaji | ................. | G02B 6/3849 372/33 |
| 6,004,043 A * | 12/1999 | Abendschein | ....... | G02B 6/3825 385/76 |
| 7,930,927 B2 | 4/2011 | Cooper et al. | | |
| 8,493,219 B2 | 7/2013 | Buck et al. | | |

(Continued)

OTHER PUBLICATIONS

U.S. Appl. No. 13/919,862, filed Jun. 17, 2013, Newell et al.
U.S. Appl. No. 14/966,135, filed Dec. 11, 2015, Melton.

*Primary Examiner* — Sang Nguyen
(74) *Attorney, Agent, or Firm* — Hamilton DeSanctis & Cha

(57) ABSTRACT

The present invention is related to monitoring movement, and in particular to systems and methods for securing a monitoring device to a monitor target.

23 Claims, 6 Drawing Sheets

(56) References Cited

U.S. PATENT DOCUMENTS

| | | |
|---|---|---|
| 8,576,065 B2 | 11/2013 | Buck et al. |
| 8,629,776 B2 | 1/2014 | Buck et al. |
| 8,657,744 B2 | 2/2014 | Rompa et al. |
| 9,240,118 B2 | 1/2016 | Melton |
| 9,241,659 B2 | 1/2016 | Rompa et al. |
| 2001/0041030 A1* | 11/2001 | Chen .................... G02B 6/3879 385/88 |
| 2003/0002808 A1* | 1/2003 | Lampert ............. G02B 6/3825 385/70 |
| 2003/0147597 A1* | 8/2003 | Duran ................. G02B 6/3825 385/76 |
| 2008/0057767 A1* | 3/2008 | O'Rourke .............. H01R 31/02 439/345 |
| 2010/0004518 A1* | 1/2010 | Vo ....................... A61B 5/14532 600/310 |
| 2010/0026995 A1* | 2/2010 | Merritt ............... A61B 5/14532 356/222 |
| 2010/0234722 A1* | 9/2010 | Trcka .................... A61B 5/055 600/410 |
| 2011/0124213 A1* | 5/2011 | Dekoski ........... H01R 13/62938 439/157 |
| 2011/0154887 A1 | 6/2011 | Cooper et al. |
| 2013/0006066 A1 | 1/2013 | Melton |
| 2014/0005484 A1* | 1/2014 | Charles ................. A61B 17/02 600/201 |
| 2015/0048948 A1 | 2/2015 | Buck et al. |
| 2015/0061864 A1 | 3/2015 | Buck et al. |
| 2015/0078622 A1 | 3/2015 | Buck et al. |
| 2015/0228184 A1 | 8/2015 | Buck et al. |
| 2015/0279200 A1 | 10/2015 | Buck et al. |
| 2015/0327214 A1 | 11/2015 | Buck et al. |

* cited by examiner

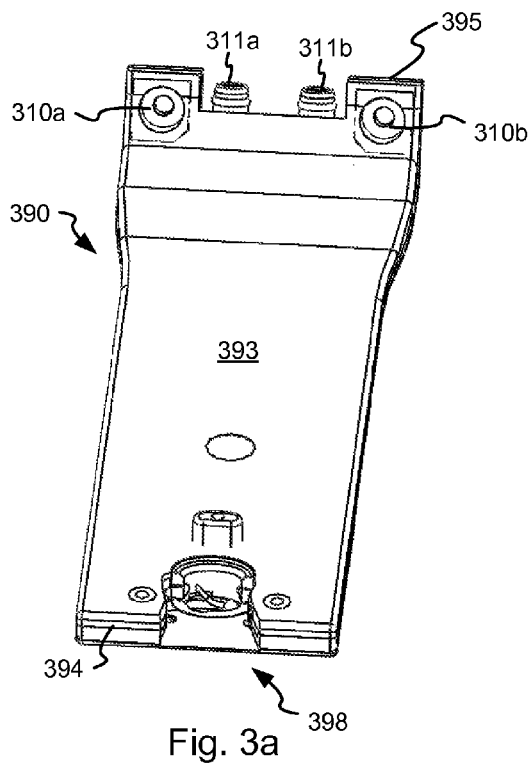
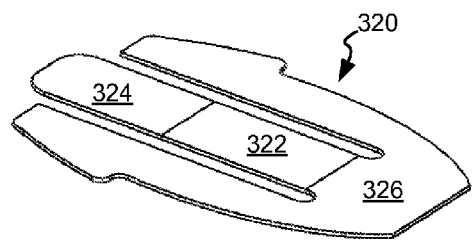
Fig. 3c
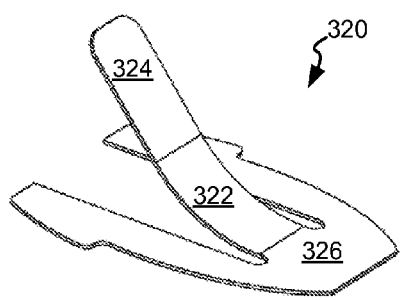
Fig. 3d
Fig. 3a
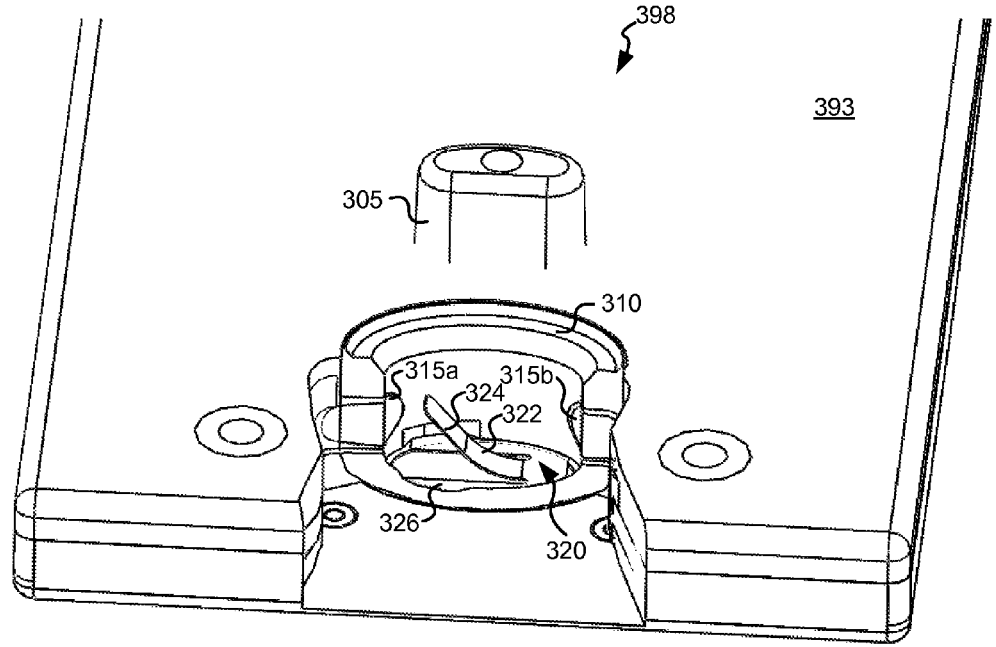
Fig. 3b

SYSTEMS AND METHODS FOR REDUCING FALSE NEGATIVE TAMPER DETECTION

CROSS REFERENCE TO RELATED APPLICATIONS

The present application claims priority to (is a non-provisional of) U.S. Pat. App. No. 61/902,754 entitled "Optical Strap Interference Flag", and filed Nov. 11, 2013 by Cooper et al. The entirety of the aforementioned provisional patent applications is incorporated herein by reference for all purposes.

BACKGROUND OF THE INVENTION

The present invention is related to monitoring movement, and in particular to systems and methods for securing a monitoring device to a monitor target.

Large numbers of individuals are currently housed in prisons. This represents a significant cost to society both in terms of housing expense and wasted productivity. To address this concern, house arrest systems have been developed for use by less violent offenders. This allows the less violent offender to be monitored outside of a traditional prison system and allows the offender an opportunity to work and interact to at least some degree in society. The same approach is applied to paroled prisoners allowing for a monitored transition between a prison atmosphere and returning to society. House arrest systems typically require attaching a monitoring device to a monitored individual. Such devices may be defeated through tampering, and as such the ability to monitor the individuals may be defeated.

Thus, for at least the aforementioned reasons, there exists a need in the art for more advanced approaches, devices and systems for individual monitoring.

BRIEF SUMMARY OF THE INVENTION

The present invention is related to monitoring movement, and in particular to systems and methods for securing a monitoring device to a monitor target.

Various embodiments of the present invention provide monitoring systems. The monitoring systems include a strap, a male connector, and an interfering element. The strap includes an optical path separated by an opening. The male connector includes an optical bridge that when inserted in the opening provides an optical bridge connecting to the optical path. The interfering element is operable to block light transmitted along the optical path when the male connector is not inserted in the opening.

This summary provides only a general outline of some embodiments according to the present invention. Many other objects, features, advantages and other embodiments of the present invention will become more fully apparent from the following detailed description, the appended claims and the accompanying drawings and figures.

BRIEF DESCRIPTION OF THE DRAWINGS

A further understanding of the various embodiments of the present invention may be realized by reference to the figures which are described in remaining portions of the specification. In the figures, similar reference numerals are used throughout several drawings to refer to similar components. In some instances, a sub-label consisting of a lower case letter is associated with a reference numeral to denote one of multiple similar components. When reference is made to a reference numeral without specification to an existing sub-label, it is intended to refer to all such multiple similar components.

FIG. 3a depicts a strap portion including an interfering element in accordance with one or more embodiments of the present invention;

FIG. 3b is a close up depiction of the strap portion of FIG. 3a showing the interfering element;

FIG. 3c shows the interfering element in a non-deployed position in accordance with one or more embodiments of the present invention;

FIG. 3d shows the interfering element in a deployed position in accordance with one or more embodiments of the present invention;

DETAILED DESCRIPTION OF THE INVENTION

The present invention is related to monitoring movement, and in particular to systems and methods for securing a monitoring device to a monitor target.

Various embodiments of the present invention provide monitoring systems. The monitoring systems include a strap, a male connector, and an interfering element. The strap includes an optical path separated by an opening. The male connector includes an optical bridge that when inserted in the opening provides an optical bridge connecting to the optical path. The interfering element is operable to block light transmitted along the optical path when the male connector is not inserted in the opening.

In some instances of the aforementioned embodiments, the interfering element is operable to deform to block the optical path when the male connector is not inserted in the opening. In various instances of the aforementioned embodiments, the interfering element is operable to move to block the optical path when no pressure is placed on the interfering element. In one or more instances of the aforementioned embodiments, a first portion of the interfering element is disposed below the optical path, and a second portion of the interfering element extends upward to block the optical path when no pressure is put on the second portion. In some such instances, the second portion is compressed downward such that it does not block the optical path when pressure is placed on the second portion. In various cases, interfering element is made of thin sheet metal with spring like characteristics.

In one or more instances of the aforementioned embodiments, the monitoring system further includes a buckle operable to connect ends of the strap, wherein the male connector is part of the buckle. In some cases, the buckle includes a securing point used to secure the buckle relative to the strap. In some instances, the strap includes connectors to connect the strap to a monitoring device.

Other embodiments of the present invention provide methods for connecting a monitoring device to a subject. Such methods include providing a strap having an optical path separated by an opening; a male connector including an optical bridge that when inserted in the opening provides an optical bridge connecting to the optical path; and an interfering element operable to block light transmitted along the optical path when the male connector is not inserted in the opening. The methods include aligning ends of the strap to align the opening with a hole; and inserting the male connector into the opening such that: the optical bridge optically connects the optical path at the opening; and the male connector moves the interfering element out of the optical path at the opening.

Figure 1:
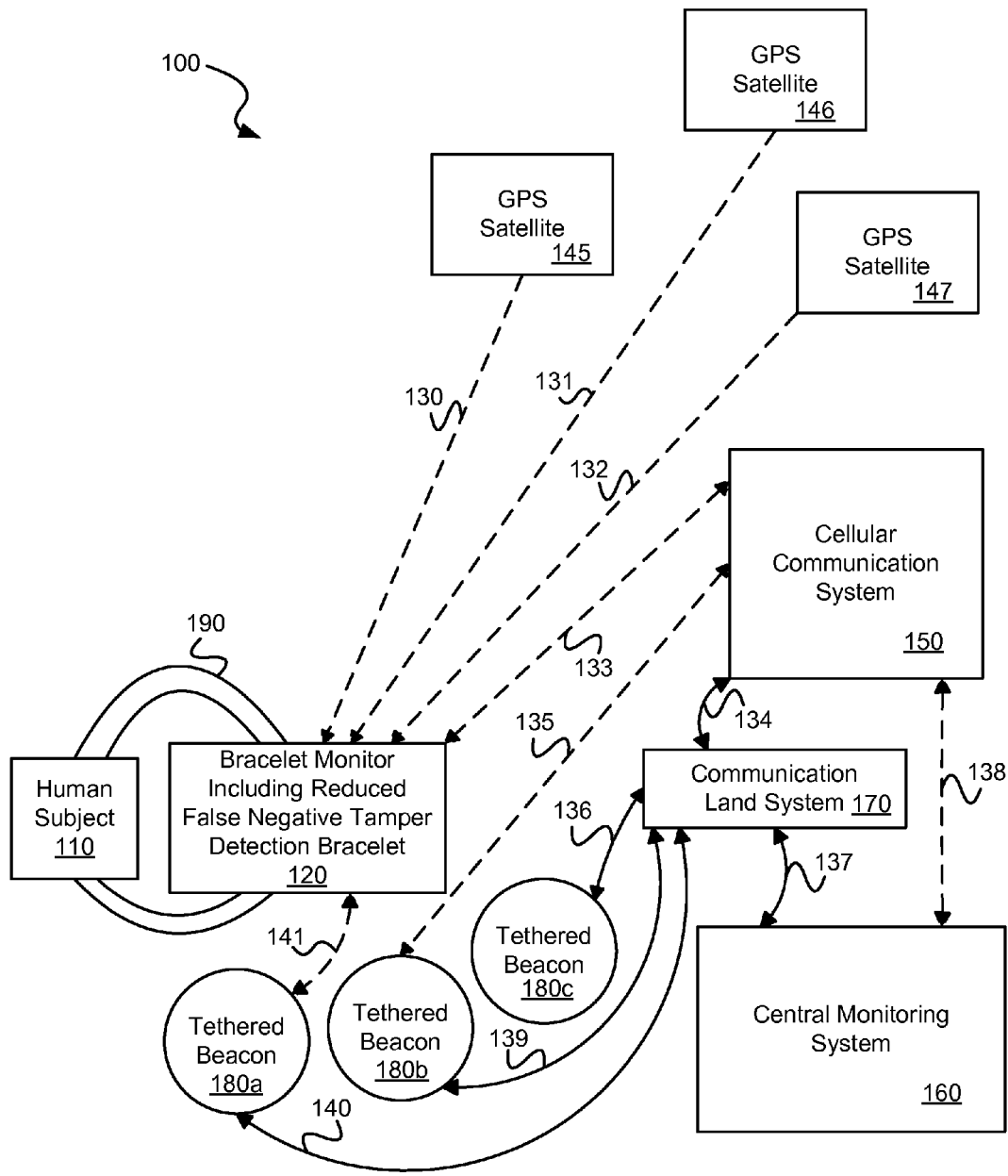
FIG. 1 is a block diagram illustrating a monitoring system including a subject device in the form of a bracelet monitor that has a reduced false negative tamper detection bracelet in accordance with various embodiments of the present invention.

Turning to FIG. 1, a tracking and monitoring system 100 including a subject device in the form of a bracelet 120 that includes a reduced false negative tamper detection bracelet in accordance with various embodiments of the present invention. Tracking and monitoring system 100 may be tailored for tracking human subjects as is referred in this detailed description. However, it should be noted that various implementations and deployments of tracking and monitoring system 100 may be tailored for tracking other animals or even inanimate objects such as, for example, automobiles, boats, equipment, shipping containers or the like.

Tracking and monitoring system 100 includes a subject device that may be, but is not limited to, a bracelet monitor 120 that is physically coupled to a human subject 110 by a securing device 190. In some cases, securing device 190 is a strap that includes a continuity sensor that when broken indicates an error or tamper condition and an interfering element that reduces the possibility of a connection being falsely reported when securing device 190 is disconnected. Further, in some cases, bracelet monitor 120 includes a proximity sensor that is able to detect when it has been moved away from an individual being monitored. When such movement away from the individual is detected, an error or tamper condition may be indicated. Such tamper detection circuitry is referred to herein as standard tamper detection circuitry. Based on the disclosure provided herein, one of ordinary skill in the art will recognize a variety of tamper sensors that may be incorporated in either bracelet monitor 120 or securing device 190 to allow for detection of removal of bracelet monitor 120 or other improper or unexpected meddling with bracelet monitor 120.

Additionally, bracelet monitor 120 may be designed to provide the location of human subject 110 under a number of conditions. For example, when bracelet monitor 120 is capable of receiving wireless GPS location information 130, 131, 132 from a sufficient number of GPS satellites 145, 146, 147 respectively, bracelet monitor 120 may use the received wireless GPS location information to calculate or otherwise determine the location of human subject 110. Alternatively or in addition, the location of a tethered beacon 180 that is local to bracelet monitor 120 may be used as the location of bracelet monitor 120. As yet another alternative, an AFLT fix may be established based on cellular communication with bracelet monitor 120. It should be noted that other types of earth based triangulation may be used in accordance with different embodiments of the present invention. For example, other cell phone based triangulation, UHF band triangulation such as Rosum, Wimax frequency based triangulation, S-5 based triangulation based on spread spectrum 900 MHz frequency signals. Based on the disclosure provided herein, one of ordinary skill in the art will recognize other types of earth based triangulation that may be used.

As yet another alternative, an AFLT fix may be established based on cellular communications between bracelet monitor 120 and a cellular communication system 150. Furthermore, when wireless communication link 133 between bracelet monitor 120 and cellular communications system 150 is periodically established, at those times, bracelet monitor 120 may report status and other stored records including location fixes to a central monitoring system 160 via wireless communication link 138.

Tracking and monitoring system 100 may include one or more tethered beacons 180. Within FIG. 1, a telemetric wireless link 141 has been depicted between tethered beacon 180a and bracelet monitor 120. Each tethered beacon 180 has an adjustable range to make telemetric wireless contact with bracelet monitor 120. At any point in time, depending on each beacon's 180 relative distance to bracelet monitor 120, none, one, or more than one tracking beacons 180 may be within transmission range of a single bracelet monitor 120. Likewise, it is further conceivable under various circumstances that more than one bracelet monitor 120 at times be within in range of a solitary tethered beacon 180.

Telemetric wireless communications path 141 established at times between tethered beacon 180a and bracelet monitor 120 illustrates a common feature of various different embodiments of the current invention. Some embodiments of the current invention vary on how, i.e. protocol, and what information and/or signaling is passed over wireless link 141. For example, in more simplified configurations and embodiments, each tethered beacon 180 is limited to repetitively transmitting its own beacon ID and motion sensor information. In that way, once bracelet monitor 120 is within transmission range of tethered beacon 180a and establishes wireless or wired reception 141, then bracelet monitor 120 can record and store received beacon ID. In particular cases where tethered beacon 180 is programmed with its physical location in addition to its beacon ID, the physical location information may also be repetitively transmitted. At a later time, for some embodiments of the present invention, bracelet monitor 120 can then report recorded readings from beacons 180 to the central monitoring system 160 over the cellular communication system 150 using wireless links 133 and 138 as depicted in FIG. 1. Furthermore, many embodiments allow for such transmissions and information passing to occur without being noticed by human subject 110, and unnoticed, automatically, and near effortlessly central monitoring system 160 is able to establish records and track human subject's 110 movements and whereabouts.

Of note, a particular tethered beacon 180 includes a beacon ID which may be, but is not limited to, a beacon identification number. This beacon identification number is transmitted to a bracelet monitor in proximity of the particular tethered beacon. This identification number may be associated with a known location of the tethered beacon. As tracking and monitoring system 100 relies on the location associated with the beacon ID provided from the tethered beacon 180 to establish the location of bracelet monitor 120, moving the particular tethered beacon away from the known location undermines the integrity of information provided from bracelet monitor 120 to central monitoring system 160. To avoid this, each of tethered beacons 180 are tethered to a fixed location power source that controls a level of motion sensing provided by the tethered beacon. Tethering beacons 180 to a power source may be done, for example, by connecting the tethered beacon to an AC wall outlet, connecting the tethered beacon to a telephone jack, connecting the tethered beacon to a cable jack, or the like. Based upon the disclosure provided herein, one of ordinary skill in the art will recognize a variety of non-movable power sources to which tethered beacons 180 may be connected in accordance with different embodiments of the present invention.

Tethered beacons 180 each include a multi-level motion sensing circuit that is operable to determine whether a respective tethered beacon 180 is moving. When a particular tethered beacon 180 is connected to a power source, a low sensitivity motion sensor circuit is employed to determine motion. In contrast, when the particular tethered beacon 180 is not connected to a power source, a high sensitivity motion sensor circuit is employed to determine motion. Thus, when tethered beacon 180 is connected to a power source and is less likely to be the subject of problematic motion (i.e., motion that impacts the integrity of location data transferred from bracelet monitor 120 to central monitoring system 160), the motion sensing employed is less sensitive. As such, the possibility of a false positive (e.g., indicating motion of the tethered beacon caused by loud music playing near the tethered beacon) when the tethered beacon 180 is unlikely to be moving is reduced. In contrast, the possibility of problematic motion is increased when tethered beacon 180 is disconnected from the power source, and in such a scenario the motion detection sensitivity is increased. In some cases, tethered beacons 180 include GPS and/or cellular communication based location circuitry that is turned on when motion is detected to obtain an updated location.

In other embodiments or configurations according to the present invention, each tethered beacon 180 also transmit status information related to its own device health and information related from each beacon's 180 internal tampering, movement, or other sensors via a communication system 170 to central monitoring system 160. This allows for detection of movement of beacons 180, and establishing some level of confidence that the physical location associated with each of beacons 180 is accurate.

Likewise, in some other embodiments, each bracelet monitor 120 contains a host of their own tampering, shielding, movement, and/or other sensors related to its own device health. While still further embodiments also include a host of other measurement transducers within bracelet monitor 120 for extracting information, and for later reporting, related to physical properties of human subject 110. For example, measuring for the presence of alcohol and/or other drugs present in human subject 110 may be included in some embodiments of bracelet monitor 120. As one example, the alcohol sensor discussed in U.S. Pat. No. 7,930,927 entitled "Transdermal Portable Alcohol Monitor and Methods for Using Such" and filed by Cooper et al. on Mar. 4, 2008. The entirety of the aforementioned reference is incorporated herein by reference for all purposes.

Tethered beacons 180 in alternative embodiments of the present invention also communicate with central monitoring system 160 independently of bracelet monitor 120. The tracking and monitoring system 100 illustrated in FIG. 1 shows tethered beacon 180b having both a wireless communication link 135 with cellular communication system 150, and also illustrates tethered beacon 180b having a hardwired communication link 139 with land communication system 170. Tracking and monitoring system 100 is also shown with tethered beacons 180a, 180b, and 180c each having hardwired land communication links 140, 139, and 136 respectively to land communication system 170. Tracking and monitoring system 100 further illustrates land communication system 170 having a hardwired communication link 134 to cellular communication system 150, and a hardwired communication link 137 to central monitoring system 160.

In some embodiments of the present invention, tethered beacons 180 are located in areas frequented by human subject 110 where bracelet monitor 120 is incapable of accessing information from the GPS system, or simply where power used accessing information from a GPS or cellular location system can be saved. Such beacons eliminate the need to perform an AFLT fix and avoid the costs associated therewith. As an example, human subject 110 may have a tethered beacon 180 placed within his home, and one also placed at his place of employment in close proximity to his work area. In this way, the two placed beacons, each at different prescribed times, can interact with his attached bracelet monitor 120 to periodically make reports to central monitoring system 160 to track movements and the whereabouts of human subject 110. All this can be done without incurring the costs associated with performing an AFLT fix.

Figure 2:
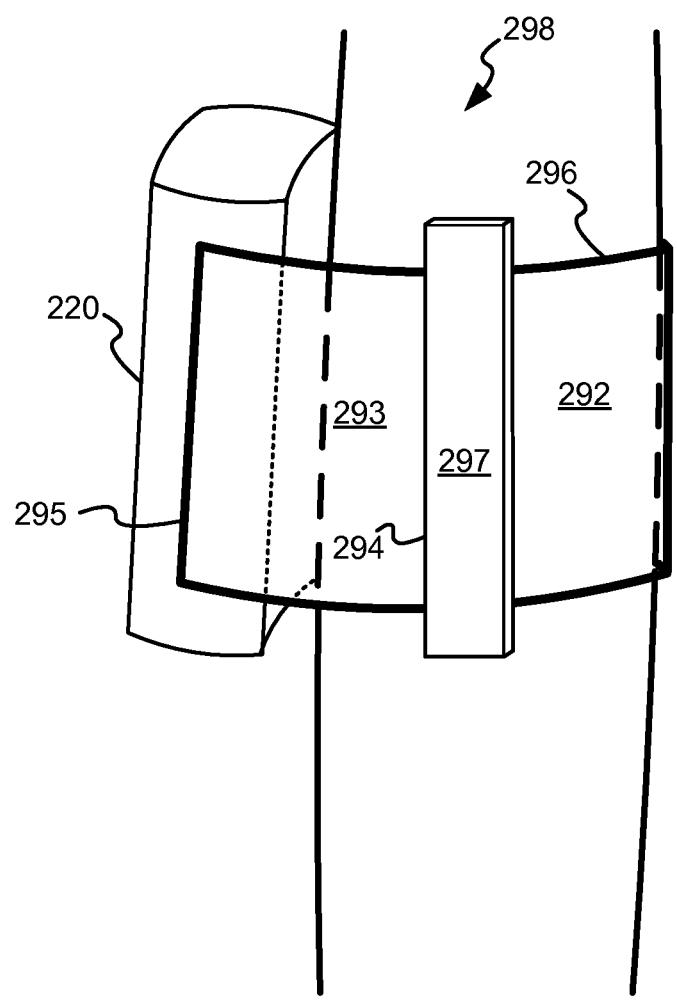
FIG. 2 shows a bracelet monitoring system installed on a human leg.

Turning to FIG. 2, a subject device 220 is shown deployed against a leg 298 of a monitored individual. As shown, a strap 296 holds subject device 220 in place against leg with a buckle 297 securing a first strap end 293 to a second strap end 292. An end 295 of strap 296 is connected to subject device 220 and an end 294 of strap 296 attaches to buckle 297.

Turning to FIG. 3a, a strap portion 390 is shown that includes an interfering element 320 in accordance with one or more embodiments of the present invention. Strap portion 390 includes a strap body 393 that may be made of, for example, a durable and flexible material allowing strap portion 393 to bend around an appendage of a monitor target. In one particular embodiment of the present invention, strap body is made of rubber. A strap end 394 is designed to align with another strap portion (not shown) when a monitor device (not shown) is connected to a monitor target. Strap end 394 includes a mating portion 398. A strap end 395 is designed to connect to a monitor device via connectors 310, 311.

Turning to FIG. 3b, a close up depiction of strap portion 390 is shown with a focus on mating portion 398 on strap end 394. As shown, mating portion 398 includes a male connector 305 extending from the surface of strap body 393 that mates into a corresponding hole on a paired strap portion (not shown). Mating portion 398 further includes a female connector 310 which is an opening into which a male connector of the paired strap portion may be pressed. Optical connections 315a, 315b are disposed on either side of female connector 310. Optical connections 315a, 315b may be made of fiber optic material and are designed to transmit a light signal. The male connector of the paired strap portion includes a fiber optic material passing there through and making a light path (i.e., an optical path) such that when the male connector is inserted into female connector 310, light transmits via the light path from optical connection 315a to/from optical connection 315b.

When the male connector of the paired strap is removed from female connector 310 it may be possible for light emitted from, for example, optical connection 315a to be received by optical connection 315b where the light transmission is facilitated through the atmosphere of female connector 310. To avoid this possibility resulting in a false negative suggesting a connection remains when in fact the connection has been opened, interfering element 320 is employed. Interfering element 320 extends upward from its base 326 when the male connector from the paired strap is removed from female connector 310. In this upward extended position, a tongue (made of two sections 322, 324) of interfering element 320 blocks any possible light transmission between optical connection 315a and optical connection 315b. Sections 322, 324 may be made of different materials causing the deformation of the tongue when the pressure of the male connector of the paired strap is removed. In one particular embodiment of the present invention, the tongue of interfering element 320 is made of thin sheet metal with spring like characteristics.

Turning to FIG. 3c, interfering element 320 is shown in a non-deployed position (i.e., a position where the tongue is depressed to be substantially aligned with base 326) which occurs when the male connector of the paired strap portion is inserted into female connector 310. By pressing the male connector of the paired strap portion is inserted into female connector 310, the male connector presses down on the tongue of interfering element 320 forcing it to be substantially in the same plane as base 326. Turning to FIG. 3d, interfering element 320 is shown in a deployed position (i.e., a position where the tongue is extended (i.e., in its free state) to obscure a light path between optical connector 315a and optical connector 315b) which occurs when the male connector of the paired strap portion is removed from female connector 310. By removing the male connector of the paired strap portion from female connector 310, the pressure on the tongue of interfering element 320 is removed and the natural propensity for the tongue to curl as shown in the figure causes the tongue to extend upward away from base 326 and thereby blocking a light path between optical connector 315a and optical connector 315b.

Figure 3E:
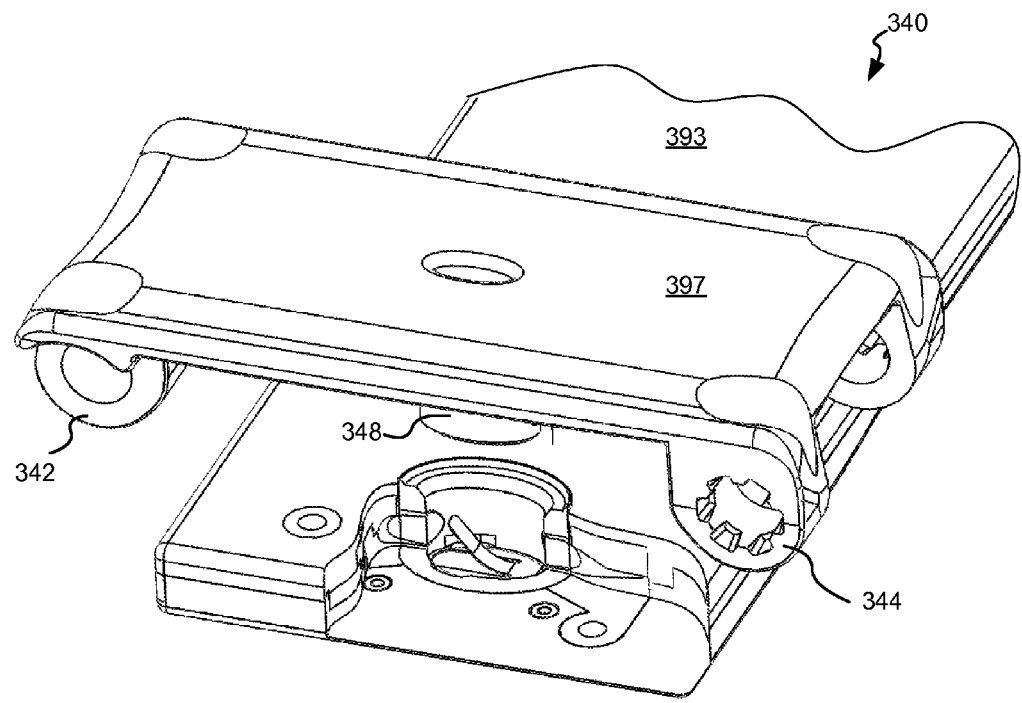
FIGS. 3e-3f show a strap portion in relation to a non-deployed buckle having a male connector operable to depress the interfering element when the buckle is deployed.
Figure 3F:
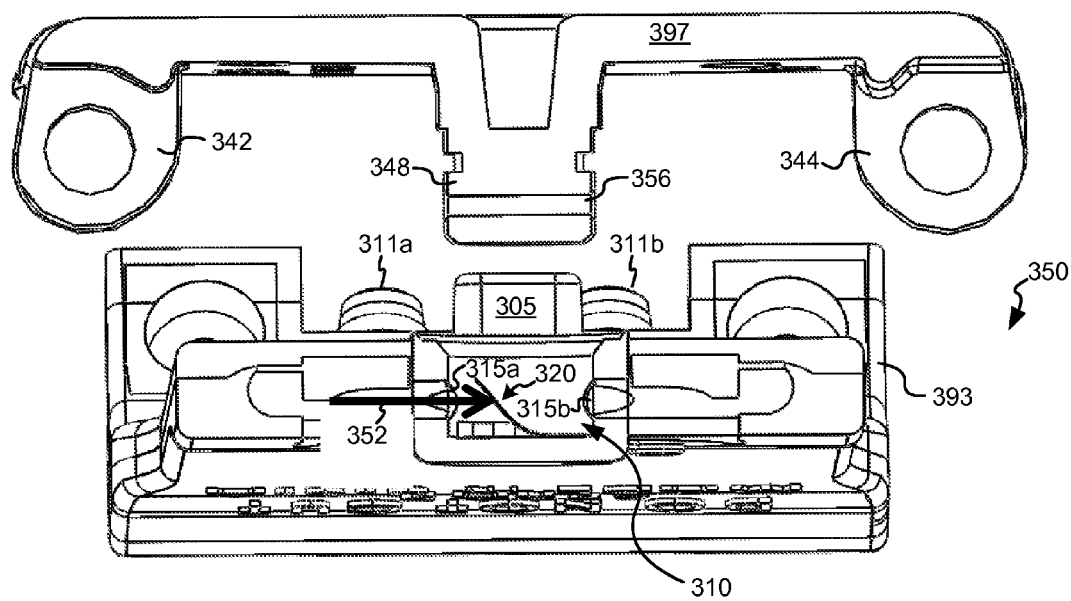

Turning to FIGS. 3e and 3f, two different views 340, 350 of a strap portion are shown in relation to a non-deployed (i.e., not connected to the strap portions) buckle 397 having a male connector 348 operable to depress interfering element 320 when buckle 397 is deployed (i.e., connected to the strap portions). Buckle 397 includes securing points 342, 344 that are used to secure buckle 397 in place when male connector 348 is inserted into female connector 310. As shown, male connector 348 of buckle 397 is aligned with holes in paired straps over female connector 310. Male connector 397 includes a light path 356 made of a fiber optic material that when male connector 348 is inserted into female connector 310 completes the optical path. When male connector 348 is removed from female connector 310 as is shown in the figures, the tongue of interfering element 320 extends upward to block a light transmission 352 from optical connector 315a from reaching optical connector 315b. As such, the possibility for a light transmission from optical connector 315a reaching optical connector 315b is greatly reduced, and thereby the possibility of a false negative tamper indication is reduced. As used herein, the phrase "false negative" is used in its broadest sense to mean a failure to indicate an actual disconnect or tamper of a strap.

Figure 3G:
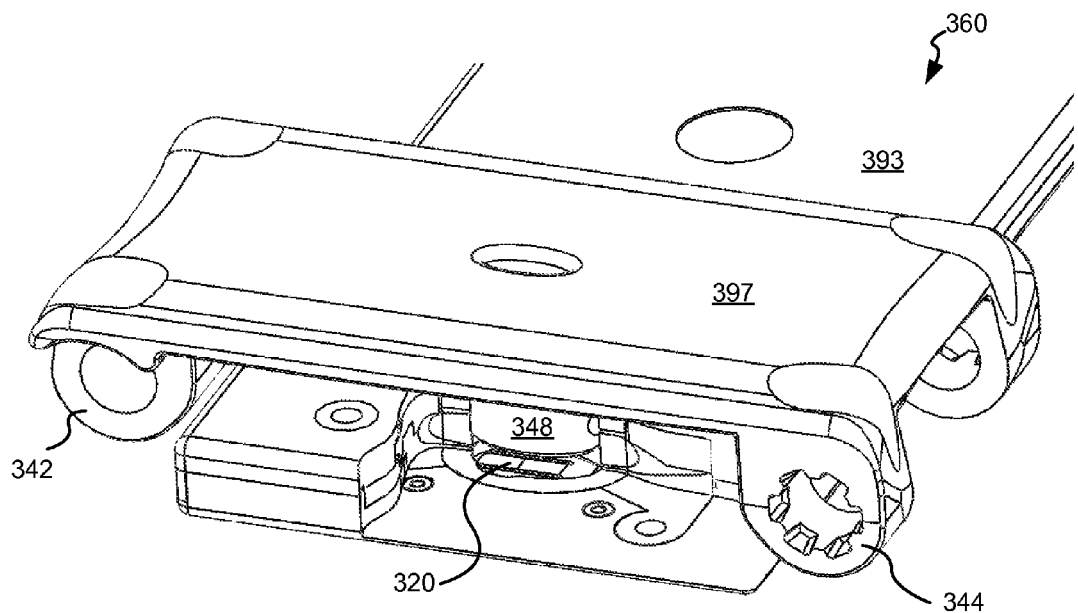
FIGS. 3g-3h show the strap portion in relation to a deployed buckle having a male connector that has depressed the interfering element.
Figure 3H:
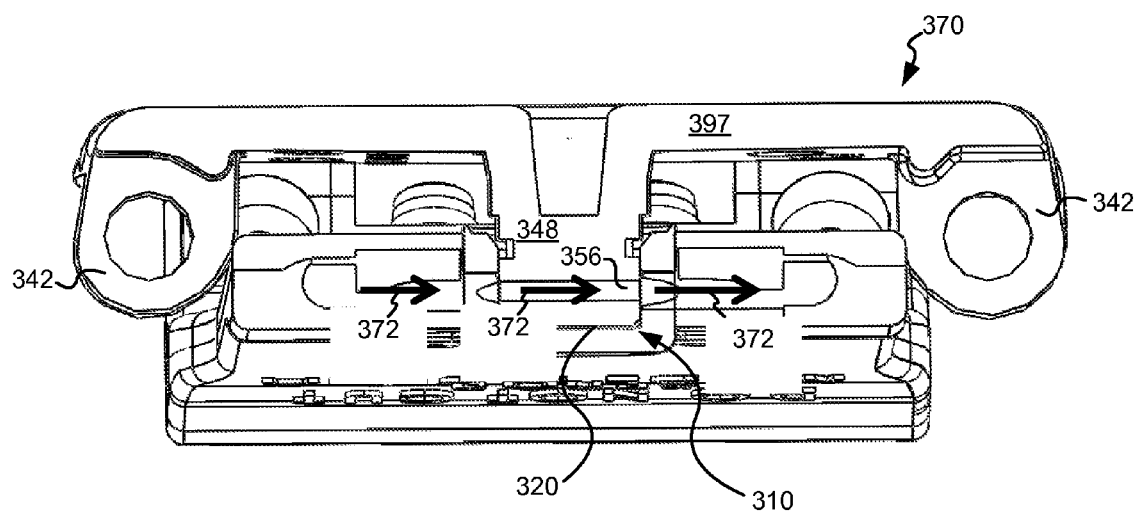

Turning to FIGS. 3g-3h show two different views 360, 370 of the strap portion in relation to a deployed buckle having a male connector that has depressed the interfering element. As shown, when deployed male connector 348 is inserted into female connector such that the tongue of interfering element 320 is depressed and light path 356 is aligned with optical connector 315a and optical connector 315b allowing for a light transmission 372 to traverse light path 356 from optical connector 315a to optical connector 315b and indicating that the strap is connected.

Figure 4:
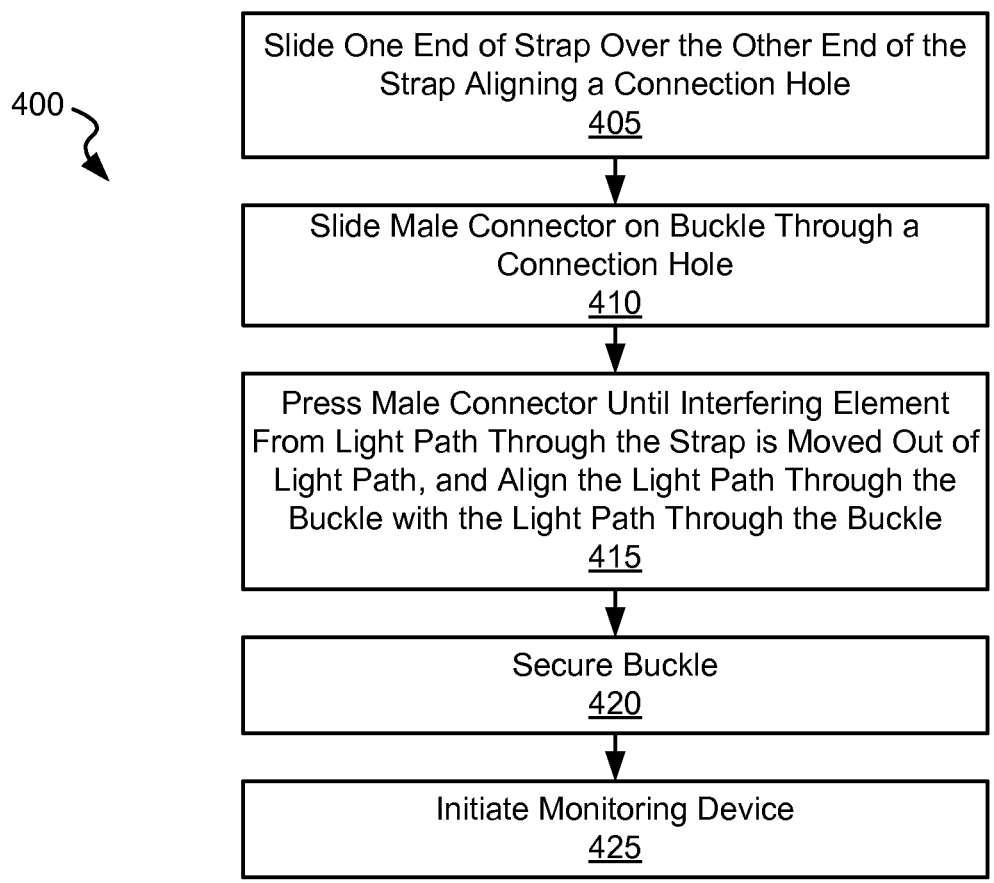
FIG. 4 is a flow diagram depicting a method for reduced false negative tamper detection in accordance with some embodiments of the present invention.

Turning to FIG. 4, a flow diagram 400 depicting a method for reduced false negative tamper detection in accordance with some embodiments of the present invention. Following flow diagram 400, one end of a strap is slid over another end of a strap such that an open ended connection hole on one strap end is aligned with a closed ended connection hole on the other strap end (block 405). A male connector on a buckle is slid through the aligned connection holes connecting the two strap ends (block 410). The male connector is pressed into the closed ended connection hole until an interfering element is pressed against the bottom of the closed ended connection hole and a light path through the male connector is aligned with optical connectors on either side of the closed ended connection hole (block 415). In this configuration, a light transmission can pass from one optical connector to the other optical connector via the light path. The buckle is then secured in place against the strap ends (block 420), and the monitoring device is initiated (block 425).

In conclusion, the present invention provides for novel systems, devices, and methods for monitoring individuals and/or assets. While detailed descriptions of one or more embodiments of the invention have been given above, various alternatives, modifications, and equivalents will be apparent to those skilled in the art without varying from the spirit of the invention. Therefore, the above description should not be taken as limiting the scope of the invention, which is defined by the appended claims.

What is claimed is:

1. A monitoring system, the monitoring system comprising:
    a strap including an optical path having a first end and a second end separated by an opening;
    a male connector including a light path distinct from the optical path that when inserted in the opening allows for light to transmit between the first end and the second end of the optical path; and
    an interfering element operable to block light transmitted along the optical path when the male connector is not inserted in the opening.

2. The monitoring system of claim 1, wherein the interfering element is operable to deform to block the optical path when the male connector is not inserted in the opening.

3. The monitoring system of claim 1, wherein the interfering element is operable to move to block the optical path when no pressure is placed on the interfering element.

4. The monitoring system of claim 1, wherein a first portion of the interfering element is disposed below the optical path, and a second portion of the interfering element extends upward to block the optical path when no pressure is put on the second portion.

5. The monitoring system of claim 4, wherein the second portion is compressed downward such that it does not block the optical path when pressure is placed on the second portion.

6. The monitoring system of claim 1, wherein the monitoring system further comprises:
    a buckle operable to connect ends of the strap, wherein the male connector is part of the buckle.

7. The monitoring system of claim 6, wherein the buckle includes a securing point used to secure the buckle relative to the strap.

8. The monitoring system of claim 1, wherein the strap includes connectors to connect the strap to a monitoring device.

9. The monitoring system of claim 1, wherein the interfering element is made of thin sheet metal with spring like characteristics.

10. The monitoring system of claim 1, wherein the light path is made of a fiber optic material.

11. The monitoring system of claim 1, wherein the light path has a first light path end and a second light path end, and wherein when the male connector is inserted in the opening, the first light path end contacts the first end of the optical path and the second light path end contacts the second end of the optical path.

12. A method for connecting a monitoring device to a subject, the method comprising:
providing a strap including:
an optical path separated by an opening, wherein the optical path has a first end on a first side of the opening and a second end on a second side of the opening;
a male connector including a fiber optic light path that when inserted in the opening allows light to transmit between the first end and the second end of the optical path;
an interfering element operable to block light transmitted along the optical path when the male connector is not inserted in the opening
aligning ends of the strap to align the opening with a hole;
inserting the male connector into the opening such that:
the fiber optic light path optically connects the first end and the second end of the optical path; and
the male connector moves the interfering element out of the optical path at the opening.

13. The method of claim 12, wherein the interfering element is made of thin sheet metal with spring like characteristics.

14. The method of claim 12, wherein the interfering element is operable to deform to block the optical path when the male connector is not inserted in the opening.

15. The method of claim 12, wherein the interfering element is operable to move to block the optical path when no pressure is placed on the interfering element.

16. The method of 10, wherein a first portion of the interfering element is disposed below the optical path, and a second portion of the interfering element extends upward to block the optical path when no pressure is put on the second portion.

17. The method of claim 16, wherein the second portion is compressed downward such that it does not block the optical path when pressure is placed on the second portion.

18. The method of claim 12, wherein the male connector is part of a buckle, and wherein inserting the male connector into the opening includes installing the male connector relative to the strap.

19. A tamper resistant strap, the strap comprising:
an optical path separated by an opening, wherein two ends of the optical path are exposed at the opening;
a male connector including a light path that when inserted in the opening provides an optical bridge connecting the optical path; and
an interfering element operable to block light transmitted along the optical path when the male connector is not inserted in the opening, wherein a first portion of the interfering element is disposed out of the optical path, and a second portion of the interfering element extends to block the optical path when no pressure is put on the second portion.

20. The strap of claim 19, wherein the means for blocking is a metal element that compresses under pressure, and does not block the optical path when sufficiently compressed.

21. The strap of claim 19, wherein the means for blocking is a metal element that extends to block the optical path in the absence of pressure.

22. The strap of claim 19, the tamper resistant strap further comprises:
a buckle operable to connect ends of the strap, wherein the male connector is part of the buckle, and wherein the buckle includes a securing point used to secure the buckle relative to the strap.

23. A signal transmitting device, the device comprising:
a component including a female connector and an optical path, wherein a first end of the optical path is accessible at a first side of the female connector and a second end of the optical path is accessible at a second side of the female connector;
a male connector including a fiber optic light path separate from the optical path, wherein when the male connector is inserted in the female connector allows for light to transmit between the first end of the optical path and the second end of the optical path; and
an interfering element operable to block light transmitted along the optical path when the male connector is not inserted in the female connector.

* * * * *